US012558497B2

(12) United States Patent
Creedon

(10) Patent No.: US 12,558,497 B2
(45) Date of Patent: Feb. 24, 2026

(54) LEAK CONTROL SYSTEM FOR AN INSUFFLATION SYSTEM, AND A METHOD FOR MINIMISING LEAKAGE FROM AN INSUFFLATION SYSTEM

(71) Applicant: PALLIARE LIMITED, Galway (IE)

(72) Inventor: Conor Creedon, Galway (IE)

(73) Assignee: Palliare Limited, Galway (IE)

( * ) Notice: Subject to any disclaimer, the term of this patent is extended or adjusted under 35 U.S.C. 154(b) by 1024 days.

(21) Appl. No.: 17/596,236

(22) PCT Filed: Jun. 15, 2020

(86) PCT No.: PCT/EP2020/066451
§ 371 (c)(1),
(2) Date: Dec. 6, 2021

(87) PCT Pub. No.: WO2020/249813
PCT Pub. Date: Dec. 17, 2020

(65) Prior Publication Data
US 2022/0305217 A1 Sep. 29, 2022

(30) Foreign Application Priority Data
Jun. 13, 2019 (IE) ..................................... 2019/0090

(51) Int. Cl.
*A61M 39/24* (2006.01)
*A61M 13/00* (2006.01)
(Continued)

(52) U.S. Cl.
CPC .......... *A61M 13/003* (2013.01); *A61M 39/24* (2013.01); *A61B 18/02* (2013.01);
(Continued)

(58) Field of Classification Search
CPC ............. A61B 18/02; A61B 2218/006; A61M 13/003; A61M 16/009; A61M 16/0858;
(Continued)

(56) References Cited

U.S. PATENT DOCUMENTS

| | | | |
|---|---|---|---|
| 10,086,166 B1 | 10/2018 | Nashed | |
| 2015/0045825 A1* | 2/2015 | Caplan | .............. A61M 25/0074 |
| | | | 606/191 |
| 2019/0060585 A1 | 2/2019 | O'Dea | |

FOREIGN PATENT DOCUMENTS

| | | |
|---|---|---|
| DE | 38 02 873 A1 | 12/1988 |
| EP | 1 177 808 A1 | 2/2002 |

(Continued)

OTHER PUBLICATIONS

International Search Report for PCT/EP2020/066451 dated, Sep. 24, 2020 (PCT/ISA/210).

(Continued)

*Primary Examiner* — Khadijeh A Vahdat
(74) *Attorney, Agent, or Firm* — Sughrue Mion, PLLC

(57) ABSTRACT

A leak control system (26) for an evacuation system (12) of an insufflation system (1), for controlling leakage of insufflating gas from a vessel (5) of a subject being insufflated. An evacuation conduit (20) connects a Venturi vacuum creating device (14) to the vessel (5) through a pressure relief valve (27) operable from a closed state to an open state in response to a pressure drop across the pressure relief valve (27) in the direction of the arrow A exceeding a predefined pressure drop value. The vacuum creating device (14) is operable in response to a signal from a pressure sensor (10) detecting pressure in the cavity (5) exceeding a predefined pressure value for applying a vacuum to the evacuating conduit (20) to increase the pressure drop across the pressure relief valve (27) to the predefined pressure drop value, for in turn operating the pressure relief valve (27) into the open state.

(Continued)

Figure 1:
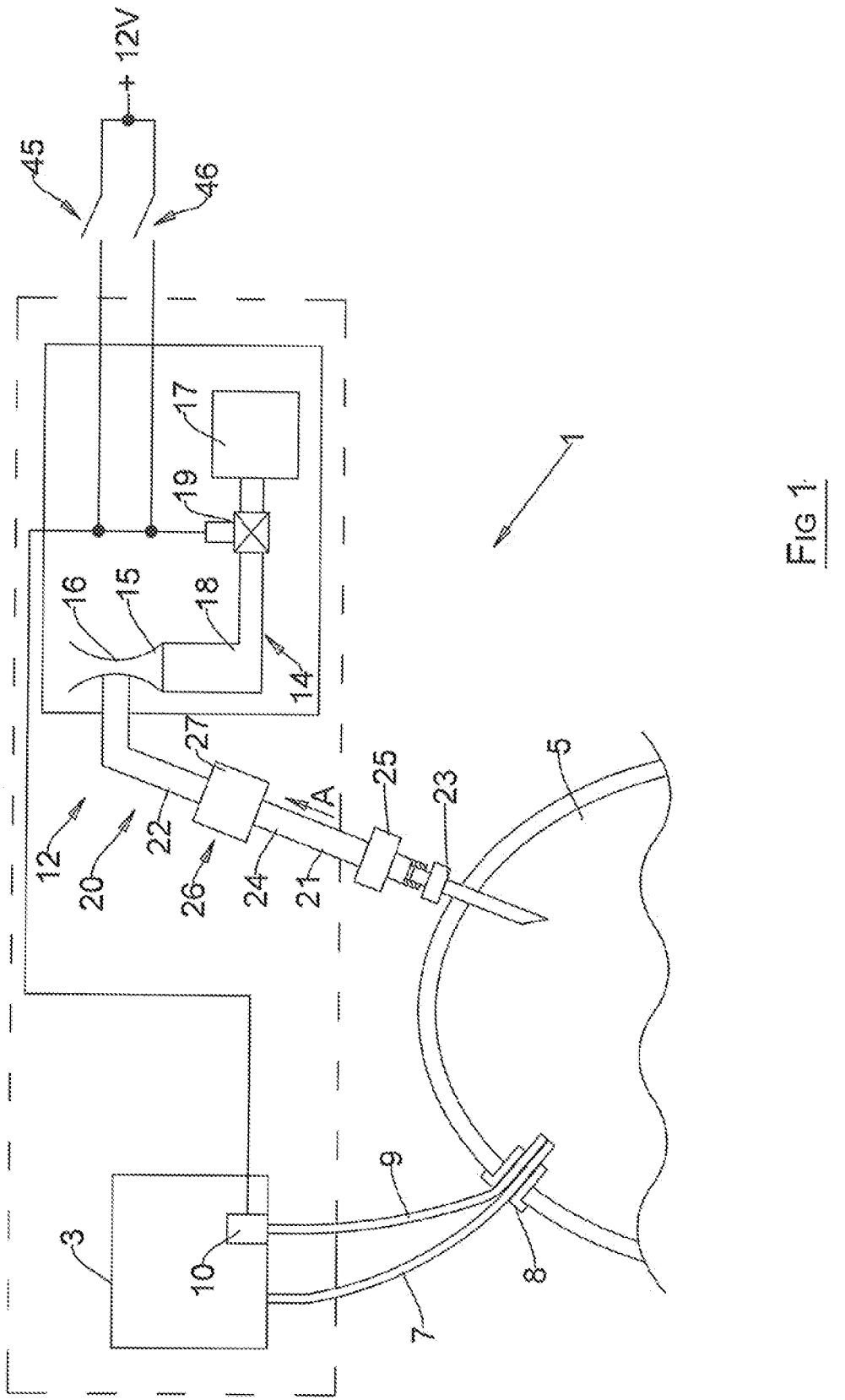

On the pressure in the vessel (5) being reduced below the predefined pressure value, the vacuum creating device (14) is deactivated, and the pressure relief valve (27) transitions into the closed state, thereby preventing further leakage of insufflating gas though the Venturi vacuum creating device (14).

20 Claims, 3 Drawing Sheets

(51) Int. Cl.
*A61M 16/20* (2006.01)
*A61B 18/02* (2006.01)

(52) U.S. Cl.
CPC .. *A61B 2218/006* (2013.01); *A61M 2039/242* (2013.01); *A61M 2205/071* (2013.01); *A61M 2205/078* (2013.01); *A61M 2206/20* (2013.01)

(58) Field of Classification Search
CPC .............. A61M 16/202; A61M 16/209; A61M 2016/0027; A61M 2202/0225; A61M 2205/07; A61M 2205/071; A61M 2205/078; A61M 2205/3334; A61M 2205/3344; A61M 2205/7509; A61M 2205/7518; A61M 2206/20
USPC .............. 606/108, 145; 600/104; 604/19, 26
See application file for complete search history.

(56) References Cited

FOREIGN PATENT DOCUMENTS

| | | | |
|---|---|---|---|
| EP | 3 009 077 | A1 | 4/2016 |
| GB | 2 164 571 | A | 3/1986 |
| GB | 2 382 639 | A | 6/2003 |
| WO | 2012/058720 | A1 | 5/2012 |
| WO | 2016/071893 | A1 | 5/2016 |
| WO | 2017/177069 | A1 | 10/2017 |
| WO | 2018/039239 | A1 | 3/2018 |
| WO | 2020/176288 | A1 | 9/2020 |

OTHER PUBLICATIONS

Written Opinion of the International Searching Authority for PCT/EP2020/066451 dated, Sep. 24, 2020 (PCT/ISA/237).

* cited by examiner

LEAK CONTROL SYSTEM FOR AN INSUFFLATION SYSTEM, AND A METHOD FOR MINIMISING LEAKAGE FROM AN INSUFFLATION SYSTEM

CROSS REFERENCE TO RELATED APPLICATIONS

This application is a National Stage of International Application No. PCT/EP2020/066451 filed Jun. 15, 2020, claiming priority based on Irish Patent Application No. S2019/0090 filed Jun. 13, 2019.

The present invention relates to a leak control system for an insufflation system, and in particular to a leak control system for minimising leakage of insufflating gas through a vessel evacuation system of an insufflation system, and the invention also relates to a method for minimising leakage of insufflating gas from an insufflation system, and in particular, for minimising leakage of insufflating gas from a vessel evacuation system of an insufflation system. The invention also relates to a vessel evacuation system, and to an insufflation system. Additionally, the invention relates to a method for minimising leakage of insufflating gas from an insufflation system, as well as to a method for insufflating a vessel of a subject.

Insufflation systems are used for insufflating a cavity, vessel or lumen in which a surgical or investigative procedure is being carried out, for example, by laparoscopic surgery or by other appropriate minimal invasive surgical or investigative means. The cavity, vessel or lumen is maintained insufflated by the insufflation system, which delivers an insufflating gas into the cavity, vessel or lumen. Pressure in the cavity, vessel or lumen is monitored during the insufflating thereof, and the flow of the insufflating gas delivered by the insufflation system to the cavity, vessel or lumen is controlled in response to the monitored pressure, in order to maintain the pressure of the insufflating gas in the cavity, vessel or lumen at a predefined pressure, which typically, is selectable.

When the pressure of the insufflating gas in the cavity, vessel or lumen is relatively low, for example, at the commencement of insufflating of the cavity, vessel or lumen, the flow rate at which the insufflating gas is delivered to the cavity, vessel or lumen by the insufflation system is relatively high. This can be problematical if the pressure of the insufflating gas in the cavity, vessel or lumen reaches the predefined pressure relatively quickly, since it is possible that before the insufflating gas can be throttled back or isolated from the cavity, vessel or lumen, the pressure in the cavity, vessel or lumen may have significantly exceeded the predefined pressure. This would be so, particularly in the case of a relatively small cavity, vessel or lumen. Accordingly, in certain cases, depending on the nature of the cavity, vessel or lumen, and the extent to which the predefined pressure has been exceeded can result in serious consequences, indeed, to the extent that a cavity, vessel or lumen may be ruptured. This is particularly so in cases where the cavity, vessel or lumen is relatively well sealed, and there is no escape for the insufflating gas in the event of the predefined pressure being exceeded. Thus, in such cavities, vessels or lumens, once the predefined pressure has been exceeded, it is difficult to reduce the pressure of the insufflating gas in the cavity, vessel or lumen.

In such insufflation systems, it is known to provide an evacuation system, for example, for evacuating smoke and other gases resulting, for example, from cauterising tissue and the like in the cavity, vessel or lumen. Such evacuation systems in general include a vacuum creating means, for example, a Venturi vacuum creating means comprising a Venturi throat, in which the vacuum is created. The vacuum creating Venturi throat is connected through an evacuating conduit to the cavity, vessel or lumen for drawing a vacuum in the cavity, vessel or lumen, to in turn draw the smoke or other gases from the cavity, vessel or lumen. The evacuating conduit may be entered into or connected to the cavity, vessel or lumen through, for example, a trocar, a Veress needle, a cannula or other suitable connecting means. In general, the Venturi vacuum creating device creates a vacuum in the Venturi throat of approximately 50 mmHg.

However, when the Venturi vacuum device is deactivated, a leakage path remains open from the cavity, vessel or lumen through the evacuating conduit, and into the Venturi throat, from which the insufflating gas leaks to atmosphere. This, therefore, results in a continuous leakage of insufflating gas from the cavity, vessel or lumen during periods where evacuation of insufflating gas from the cavity, vessel or lumen is not required. A similar problem can arise with other vacuum creating means, for example, some vacuum pumps.

There is therefore a need for a leak control system for minimising such leakage of insufflating gas, and there is also a need for an evacuation system and an insufflation system in which leakage of insufflating gas is minimised.

The present invention is directed towards providing such a leak control system, an evacuation system and an insufflation system, and the invention is also directed towards providing a method for minimising leakage of insufflating gas from an insufflation system. The present invention is also directed towards providing a method for minimising leakage of insufflating gas through a vessel evacuation system, and also to a method for insufflating a vessel of a subject.

According to the invention there is provided a leak control system for minimising leakage of insufflating gas through a vessel evacuation system of an insufflation system, the leak control system comprising a pressure relief valve located in a flow path of the evacuation system upstream of a vacuum creating means of the evacuation system, the pressure relief valve being operable from a closed state preventing gas flow to the vacuum creating means through the flow path, to an open state permitting gas flow to the vacuum creating means through the flow path, in response to a pressure drop across the pressure relief valve in the direction of flow to the vacuum creating means exceeding a predefined pressure drop value.

In one embodiment of the invention the flow path is configured to communicate the evacuation system with a vessel being insufflated.

In another embodiment of the invention the pressure relief valve is directly responsive to the pressure drop across the pressure relief valve exceeding the predefined pressure drop value in the direction of flow to the vacuum creating means to transition from the closed state to the open state.

In another embodiment of the invention the pressure relief valve comprises a valve seat defining a valve orifice therethrough for accommodating gas therethrough to the vacuum creating means, and a valving element operable between a closed state sealably engaging the valve seat to close the valve orifice with the valve in the closed state, and an open state spaced apart from the valve seat to open the valve orifice with the valve in the open state.

Preferably, the valve seat extends around the valve orifice.

Advantageously, the valving element is located on the downstream side of the valve seat.

In one embodiment of the invention the valving element is urgeable into the closed state by an urging means acting against the direction of flow to the vacuum creating means.

In one embodiment of the invention the urging means is configured to urge the valving element into the closed state with a force sufficient to maintain the valving element in the closed state until the pressure drop across the valving element in the direction of flow to the vacuum creating means exceeds the predefined pressure drop value.

In another embodiment of the invention the urging means is configured to act on the valving element for urging the valving element into the closed state.

In a further embodiment of the invention the urging means is configured to act directly on the valving element for urging the valving element into the closed state.

In another embodiment of the invention the urging means comprises a passive urging means. Preferably, the urging means comprises a spring urging means. Advantageously, the urging means comprises a spring. Ideally, the urging means comprises a compression spring.

In one embodiment of the invention the pressure relief valve is adjustable for selectively varying the predefined pressure drop value to which the pressure relief valve is responsive. Preferably, the urging means is adjustable for selectively varying the predefined pressure drop value to which the pressure relief valve is responsive. Advantageously, the urging means is adjustable for selectively varying the force with which the urging means urges the valving element into the closed state.

In one embodiment of the invention the urging means acts against an anchoring means for urging the valving element into the closed state. Preferably, the urging means is located between the anchoring means and the valving element. Advantageously, the urging means acts between the anchoring means and the valving element. Ideally, the anchoring means is moveable for varying the force with which the urging means urges the valving element into the closed state.

In one embodiment of the invention the anchoring means is moveable relative to the valving element for varying the force with which the urging means urges the valving element into the closed state. Preferably, the anchoring means is moveable relative to the valving element for varying the spacing between the anchoring means and the valving element.

In another embodiment of the invention a means for moving the anchoring means is provided. Preferably, the means for moving the anchoring means comprises a manually operable moving means.

In another embodiment of the invention the pressure relief valve comprises a housing defining a hollow interior region, a partition wall located in the hollow interior region of the housing dividing the hollow interior region into an upstream valve chamber and a downstream valve chamber, the valve orifice being formed in the partition wall and communicating the downstream valve chamber with the upstream valve chamber, an inlet port to the upstream valve chamber configured for connecting to the flow path on the upstream side of the pressure relief valve, and an outlet port from the downstream valve chamber configured for connecting to the flow path on the downstream side of the pressure relief valve.

In another embodiment of the invention the urging means is located in the downstream valve chamber, and acts on the valving element in an upstream direction.

Preferably, the anchoring means is located in the downstream valve chamber. Advantageously, the means for moving the anchoring means is accessible externally of the housing.

In one embodiment of the invention an evacuating conduit is provided, the evacuating conduit defining the flow path and terminating in an upstream end configured for receiving the insufflating gas from a vessel being insufflated. Preferably, the upstream end of the evacuating conduit is configured for communicating with the vessel.

In another embodiment of the invention the upstream end of the evacuating conduit is configured for communicating with the vessel through one of a trocar, a cannula and a Veress needle. Preferably, the evacuating conduit is configured for receiving insufflating gas and other gases from a vessel being insufflated. Advantageously, the evacuating conduit is configured for receiving insufflating gas and other gases from an adjacent vessel adjacent the vessel being insufflated.

In another embodiment of the invention the evacuating conduit is configured for communicating with the vacuum creating means of the vessel provided for delivering the insufflating gas from the evacuation system.

In a further embodiment of the invention the pressure relief valve is located in the evacuation conduit.

In one embodiment of the invention the leak control system comprises the vacuum creating means of the evacuation system.

In another embodiment of the invention the vacuum creating means comprises a Venturi vacuum creating device having a Venturi throat, and the flow path is configured to communicate with the Venturi throat of the Venturi vacuum creating device.

In one embodiment of the invention the predefined pressure drop value lies in the range of 5 mmHg to 1000 mmHg.

In another embodiment of the invention the predefined pressure drop value lies in the range of 10 mmHg to 500 mmHg.

Preferably, the predefined pressure drop value lies in the range of 15 mmHg to 50 mmHg. Advantageously, the predefined pressure drop value lies in the range of 20 mmHg to 30 mmHg. Ideally, the predefined pressure drop value is approximately 25 mmHg.

In another embodiment of the invention the vacuum creating means is configured to generate a vacuum down to 30 mmHg below atmospheric pressure. Preferably, the vacuum creating means is configured to generate a vacuum down to 50 mmHg below atmospheric pressure. Advantageously, the vacuum creating means is configured to generate a vacuum down to 500 mmHg below atmospheric pressure. Ideally, the vacuum creating means is configured to generate a vacuum down to 1000 mmHg below atmospheric pressure.

The invention also provides an evacuation system for an insufflation system, the evacuation system comprising a vacuum creating means for communicating with a vessel being insufflated through a flow path for accommodating insufflating gas from the vessel, and the leak control system according to the invention with the pressure relief valve of the leak control system being located in the flow path upstream of the vacuum creating means.

In one embodiment of the invention the vacuum creating means comprises a Venturi vacuum creating device.

In another embodiment of the invention the flow path for accommodating the insufflating gas from the vessel terminates in a vacuum generating throat of the Venturi vacuum creating device.

In another embodiment of the invention the vacuum creating means is responsive to one of a signal generated in response to pressure in the vessel being insufflated exceeding a predefined pressure value, and an externally generated signal.

In another embodiment of the invention the signal generated in response to the pressure in the vessel being insufflated exceeding the predefined pressure is generated by a pressure monitoring means.

In a further embodiment of the invention the signal generated in response to the pressure in the vessel being insufflated exceeding the predefined pressure is generated by a pressure sensor.

In another embodiment of the invention the signal generated in response to the pressure in the vessel being insufflated exceeding the predefined pressure is generated by the pressure monitoring means located in one of the vessel and remotely thereof.

In another embodiment of the invention the signal generated in response to the pressure in the vessel being insufflated exceeding the predefined pressure is produced by the insufflation system.

In one embodiment of the invention the externally generated signal comprises one of a manually generated signal, and a signal generated in response to activation of a surgical instrument.

In another embodiment of the invention the manually generated signal is generated by one of a foot operable switch and a hand operable switch.

In a further embodiment of the invention the manually generated signal is generated by both a foot operable switch and a hand operable switch.

In another embodiment of the invention the signal generated in response to activation of a surgical instrument is generated in response to a surgical instrument located in the vessel.

In another embodiment of the invention the signal generated in response to activation of a surgical instrument is generated in response to one of a cauterising instrument and a freezing instrument.

In one embodiment of the invention the signal generated in response to activation of a surgical instrument is generated in response to the cauterising instrument being activated.

In another embodiment of the invention the signal generated in response to activation of a surgical instrument is generated in response to the freezing instrument being activated.

Preferably, the freezing instrument comprises an instrument configured to deliver a liquid gas to a site to be frozen.

In one embodiment of the invention the predefined pressure lies in the range of 5 mmHg to 50 mmHg.

In another embodiment of the invention the predefined pressure lies in the range of 10 mmHg to 50 mmHg.

Preferably, the predefined pressure lies in the range of 15 mmHg to 50 mmHg. Advantageously, the predefined pressure lies in the range of 20 mmHg to 30 mmHg, and ideally, the predefined pressure is approximately 25 mmHg.

Additionally, the invention provides an insufflation system for supplying an insufflating gas to a vessel of a subject, the insufflation system comprising an evacuation system according to the invention for evacuating insufflating gas from the vessel through a flow path communicating the evacuation system with the vessel, and the leak control system located in the flow path.

Further the invention provides a method for minimising leakage of insufflating gas from an insufflation system, the method comprising locating a pressure relief valve in a flow path of a vessel evacuation system upstream of a vacuum creating means thereof, configuring the pressure relief valve to be operable from a closed state preventing gas flow to the vacuum creating means through the flow path, to an open state permitting gas flow to the vacuum creating means through the flow path, in response to a pressure drop across the pressure relief valve in the direction of flow to the vacuum creating means exceeding a predefined pressure drop value.

In one embodiment of the invention the flow path communicates the evacuation system with a vessel being insufflated.

The invention also provides a method for minimising leakage of insufflating gas through a vessel evacuation system of an insufflation system, the method comprising locating a pressure relief valve in a flow path of the vessel evacuation system upstream of a vacuum creating means of the vessel evacuation system, communicating the vessel evacuation system with the vessel through the flow path, and operating the pressure relief valve from a closed state preventing gas flow to the vacuum creating means through the flow path, to an open state permitting gas flow to the vacuum creating means through the flow path in response to a pressure drop across the pressure relief valve in the direction of flow to the vacuum creating means exceeding a predefined pressure drop value.

Preferably, the pressure relief valve is configured to be directly responsive to the pressure drop across the pressure relief valve exceeding the predefined pressure drop value for transitioning from the closed state to the open state.

Advantageously, the pressure relief valve is adjustable for selectively varying the predefined pressure drop to which the pressure relief valve is responsive.

Ideally, the pressure relief valve is manually adjustable.

In one embodiment of the invention the leak control system comprises a vacuum creating means of the evacuation system.

In another embodiment of the invention the vacuum creating means comprises a Venturi vacuum creating device having a Venturi throat, and the flow path communicates with the Venturi throat of the Venturi vacuum device.

Additionally, the invention provides a method for insufflating a vessel of a subject, the method comprising delivering an insufflating gas to the vessel of the subject, providing a flow path from the vessel to a vacuum creating means of a vessel evacuation system, locating a pressure relief valve in the flow path upstream of the vacuum creating means, and configuring the pressure relief valve to be operable from a closed state preventing gas flow to the vacuum creating means through the flow path, to an open state permitting gas flow to the vacuum creating means through the flow path in response to a pressure drop across the pressure relief valve in the direction of flow to the vacuum creating means exceeding a predefined pressure drop value.

Figure 2:
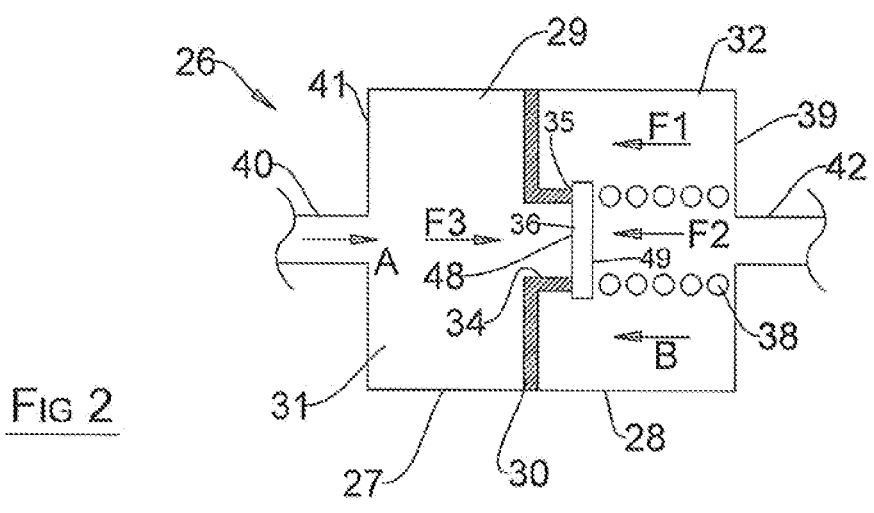
Figure 3:
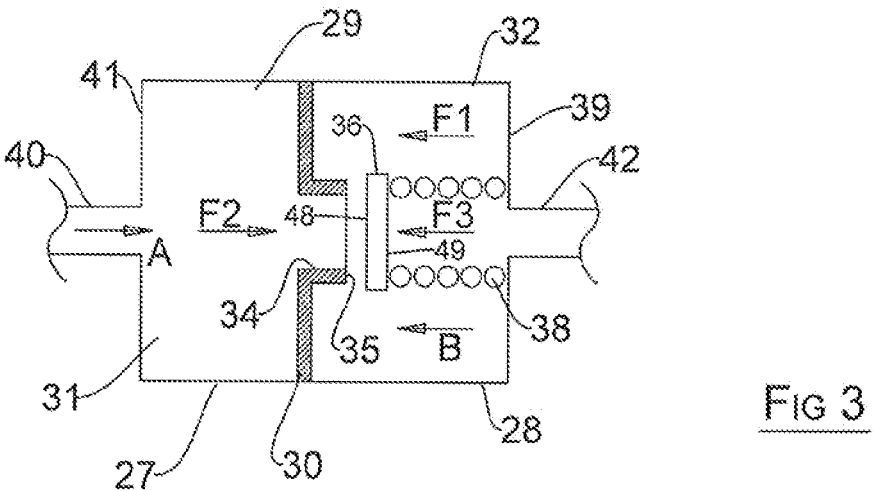
Figure 4:
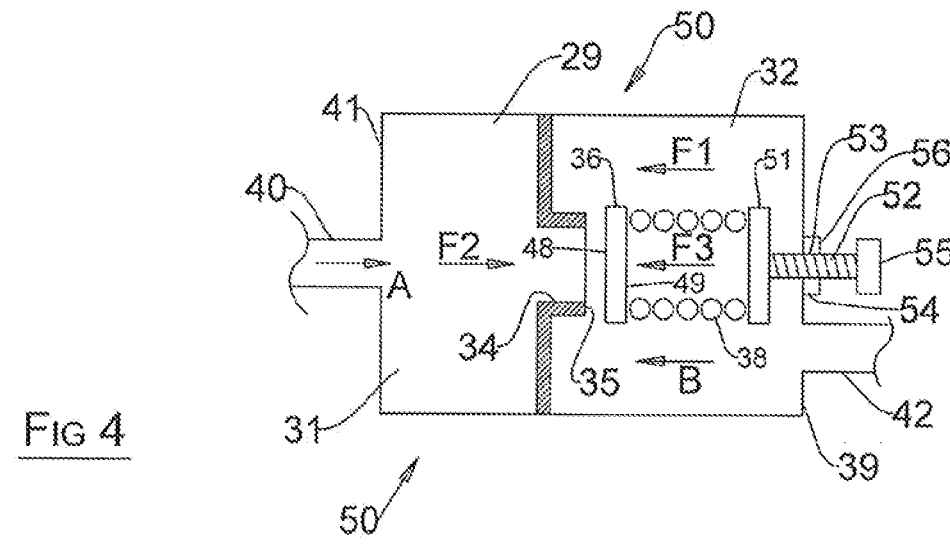
Figure 5:
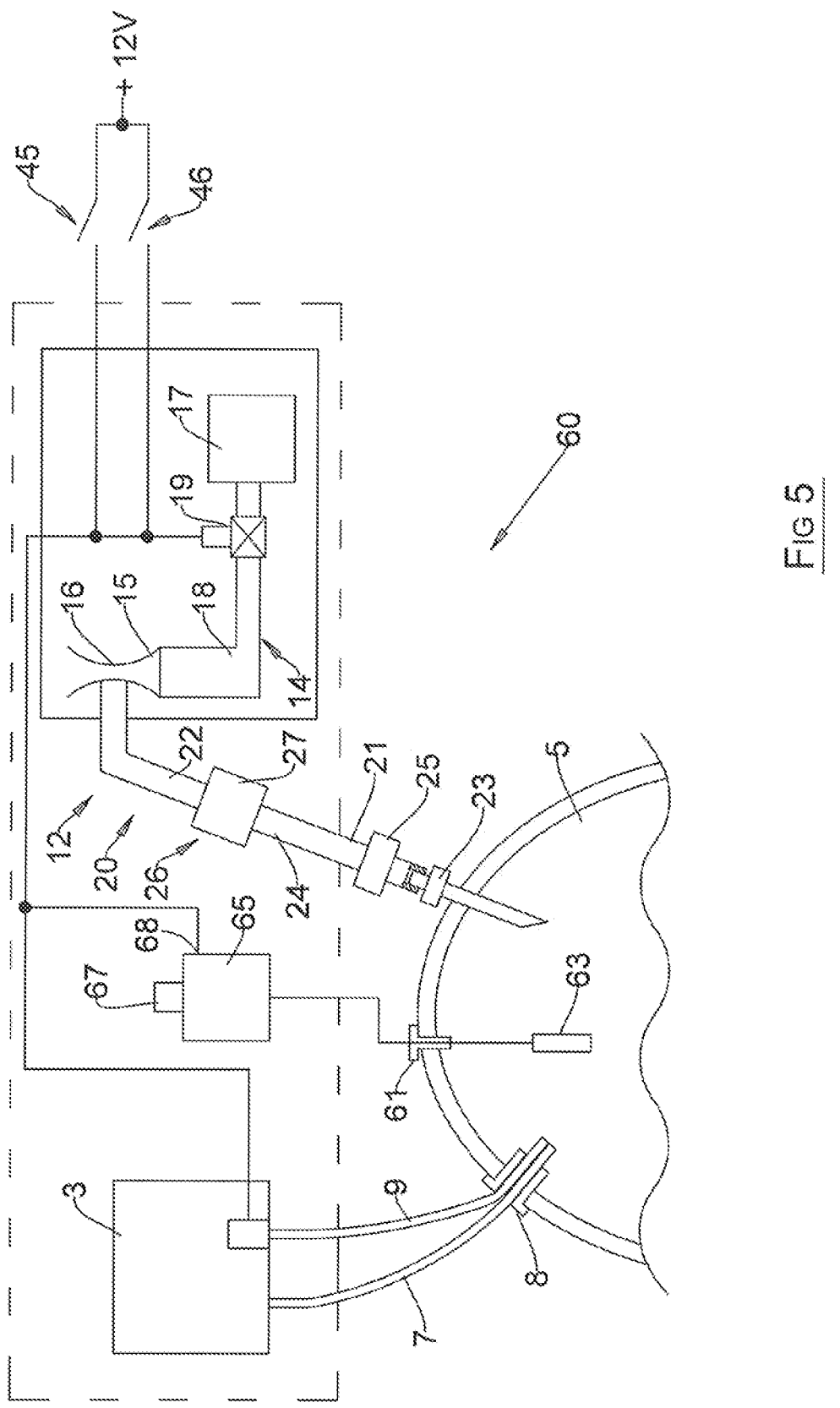

The invention will be more clearly understood from the following description of some preferred embodiments thereof which are given by way of example only with reference to the accompanying drawings, in which:

FIG. 1 is a schematic illustration of an insufflation system according to the invention for insufflating a vessel in a human or animal subject which comprises a leak control system also according to the invention of an evacuation system also according to the invention of the insufflation system, FIG. 2 is a schematic diagram of a part of the leak control system of FIG. 1, FIG. 3 is a view similar to FIG. 2 of the part of FIG. 2 in a different state to that of FIG. 2, FIG. 4 is a view similar to FIG. 3 of a part of a leak control system according to another embodiment of the invention, and FIG. 5 is a view similar to FIG. 1 of an insufflation system according to another embodiment of the invention.

Referring to the drawings and initially to FIGS. 1 to 3 thereof, there is illustrated an insufflation system according to the invention indicated generally by the reference numeral 1. The insufflation system 1 comprises and insufflator 3 for insufflating a vessel 5 of a human or animal subject with an insufflating gas and for controlling the flow rate of the insufflating gas to the vessel 1. The vessel 1 may be any cavity, vessel or lumen in a human or animal body, for example, an abdominal cavity, a rectum, a large intestine, a small intestine, a stomach, or any other cavity, vessel or lumen. The insufflating gas may be any suitable gas, and typically, is carbon dioxide. The insufflator 3 sets and controls the pressure at which the insufflating gas is delivered from the insufflator 3 to the vessel 5, and also controls the flow rate of insufflating gas from the insufflator 3 to the vessel 5. Such insufflators as the insufflator 3 will be well known to those skilled in the art, and further description should not be required.

An insufflating conduit 7 extending from the insufflator 3 accommodates the insufflating gas to the vessel 5. Typically, the insufflating conduit 7 either extends into the vessel 5 through a trocar 8, or may be connected to a trocar, which in turn would accommodate the insufflating gas from the insufflating conduit 7 into the vessel 5. Such arrangements for delivering a insufflating gas from an insufflator through an insufflating conduit to a vessel during insufflating thereof will be well known to those skilled in the art. A pressure conduit 9 extends from the insufflator 3 and into the vessel 5 through the trocar 8, or may be connected to the trocar or may extend into the vessel 5 through another trocar, cannula or a Veress needle. Such arrangements for connecting a pressure conduit with a vessel being insufflated will be well known to those skilled in the art. The pressure conduit 9, connects the vessel 5 to a pressure sensor 10 located in the insufflator 3. The gas in the pressure conduit 9 is static, so that the pressure read by the pressure sensor 10 provides a true reading of the static pressure of the insufflating gas in the vessel 5. The insufflator 3 controls the flowrate of the insufflating gas to the vessel 5 in response to the pressure read from the pressure sensor 10 for maintaining the pressure of the insufflating gas in the vessel 5 at a predefined pressure value, which in this embodiment of the invention is approximately 25 mmHg. However, the predefined pressure may be selectable, and would be selected based on the nature of the vessel being insufflated. Typically, pressures to which vessels are insufflated range from 5 mmHg to 30 mmHg, depending on the vessel being insufflated, although in some cases vessels may be insufflated to pressures up to 50 mmHg.

An evacuation system also according to the invention and indicated generally by the reference numeral 12 is provided in the insufflation system 1 for evacuating gases from the vessel 5 as will be described in more detail below. The evacuation system 12 comprises a vacuum creating means, which in this embodiment of the invention comprises a Venturi vacuum creating device 14. The Venturi vacuum creating device 14 comprises a Venturi element 15 defining a Venturi throat 16. Gas at high velocity is delivered through the Venturi element 15 from a compressed gas source 17, which may, for example, be a compressed air source. Gas from the compressed gas source 17 is delivered to the Venturi element 15 through a delivery conduit 18 under the control of a solenoid operated valve 19. The high velocity gas passing through the Venturi element 15 generates a vacuum in the Venturi throat 16, which in this embodiment of the invention is approximately 50 mmHg below atmospheric pressure, although, it is envisaged that in some embodiments of the invention the vacuum generated by the Venturi vacuum creating device may be down to 500 mmHg and even down to 1000 mmHg below atmospheric pressure.

An evacuating conduit 20 comprising an upstream portion 21 and a downstream portion 22 communicates the Venturi throat 16 of the Venturi element 15 with the vessel 5. Typically, the evacuating conduit 20 is inserted into the vessel 5 through a trocar, but in this embodiment of the invention the upstream portion 21 of the evacuating conduit 20 communicates with the vessel 5 through a Veress needle 23. The evacuating conduit 20 defines a flow path 24 therethrough, through which the Venturi throat 16 communicates with the vessel 5 for evacuating insufflating gas and other gases from the vessel 5 in the direction of the arrow A.

Such gases may, for example, be smoke which may be generated by cauterising tissue and the like within the vessel 5, or by cauterising other vessels, lumen or organs located in the vessel 5. As well as smoke, such gases may comprise, for example, nitrogen gas or other gases at relatively high pressures evaporating from liquid nitrogen or the liquid phase or other gases delivered into the vessel 5 of the subject in the liquid phase for freezing a site, tissue, a lumen or organ in the vessel 5, which could result in a rapid rise in pressure in the vessel 5 as the liquid phase of the gas transitions from the liquid phase to the gaseous phase. Additionally, such gases may, for example, be noxious gases or other noxious by-product gases found in the vessel 5.

A filter 25 located in the flow path 24 defined by the evacuating conduit 20 filters out any such noxious gases and other noxious by-products contained in the insufflating gas or smoke being drawn from the vessel 5 in the direction of the arrow A under the vacuum from the Venturi vacuum creating device 14. Additionally, the filter 25 is configured to filter out particulate matter entrained in the gas, such as organisms, for example, pathogens, infections, viruses, and the like.

Referring now to FIGS. 2 and 3, a leak control system also according to the invention and indicated generally by the reference numeral 26 for minimising leakage of insufflating gas from the vessel 5 through the evacuation system 12 when the evacuation system 12 is deactivated, comprises a pressure relief valve 27. The pressure relief valve 27 is located in the flow path 24 defined by the evacuating conduit 20 between the vessel 5 and the vacuum creating device 14 and upstream of the vacuum creating device 14, and downstream of the filter 25. The pressure relief valve 27 is operable from a closed state illustrated in FIG. 2 for preventing gas flow through the flow path 24 defined through the evacuating conduit 20, and thereby isolating the vessel 5 from the Venturi vacuum creating device 14, to an open state illustrated in FIG. 3 permitting gas flow through the flow path 24 defined by the evacuating conduit 20 in the direction of the arrow A from the vessel 5 to the Venturi vacuum creating device 14, so that when the Venturi vacuum creating device 14 is active generating a vacuum in the Venturi throat 16, insufflating gas, smoke and other gases are drawn from the vessel 5 through the evacuating conduit 20. The pressure relief valve 27 is responsive to a pressure drop developed across the pressure relief valve 27 in the direction of flow from the vessel 5 to the Venturi vacuum creating device 14, namely, in the direction of the arrow A, exceeding a predefined pressure drop value, which is discussed in more detail below, for operating from the closed state to the open state.

In this embodiment of the invention the pressure relief valve 27 comprises a valve housing 28 defining a hollow interior region, which forms a valve chamber 29. A partition wall 30 divides the valve chamber 29 into an upstream valve chamber 31 and a downstream valve chamber 32. A valve orifice 34 extending through the partition wall 30 communicates the downstream valve chamber 32 with the upstream valve chamber 31. A valve seat 35 extends around the valve orifice 34 for sealably engaging a valving element 36. The valving element 36 is urgeable in a generally upstream direction, namely, in the direction of the arrow B from an open state with the pressure relief valve 27 in the open state of FIG. 3, into a closed state sealably engaging the valve seat 35 with the pressure relief valve 27 in the closed state of FIG. 2. An urging means, which in this embodiment of the invention comprises a passive urging means, namely, a spring urging means, provided by a compression spring 38 urges the valving element 36 into the closed state sealably engaging the valve seat 35. The compression spring 38 acts between the valving element 36 and an anchoring means, which in this embodiment of the invention comprises a downstream end wall 39 of the valve housing 28 for releasably retaining the valving element 36 in the closed state.

An inlet port 40 extending from an upstream end wall 41 of the valve housing 28 is connected to the upstream portion 21 of the evacuating conduit 20 for communicating the upstream valve chamber 31 through the filter 25 to the vessel 5. An outlet port 42 extending from the downstream end wall 39 of the valve housing 28 is connected to the downstream portion 22 of the evacuating conduit 20, for communicating the downstream valve chamber 32 to the Venturi throat 16 of the Venturi vacuum device 14.

In this embodiment of the invention the compression spring 38 is configured to urge the valving element 36 into the closed state to sealably engage the valve seat 35 with a force F1. The value of the force F1 acting on the valving element 36 when the valving element 36 is in the closed state, in this embodiment of the invention, is sufficient to retain the valving element 36 in the closed state until the pressure drop across the valving element 36 in the direction of gas flow from the vessel 5 to the Venturi vacuum creating device 14, namely, in the direction of the arrow A, exceeds the predefined pressure drop value, which in this embodiment of the invention is approximately 25 mmHg. Once the pressure drop across the valving element 36 in the direction of the arrow A exceeds the predefined pressure drop value of 25 mmHg, the compression spring 38 yields thereby permitting the valving element 36 to be urged by the pressure drop across the valving element 36 in the direction of the arrow A from the closed state to the open state spaced apart from the valve seat 35 with the pressure relief valve 27 in the open state to thereby communicate the vessel 5 with the Venturi throat 16 of the Venturi vacuum creating device 14 for the evacuation of insufflating gases together with smoke and other gases to be drawn from the vessel 5 under vacuum by the Venturi vacuum creating device 14. The value of the force F, applied by the compression spring 38 to the valving element 36 is described in more detail below.

The solenoid operated valve 19 is responsive to a control signal generated in response to the pressure in the vessel 5 exceeding the predefined pressure value, or either of two externally generated control signals for applying gas from the compressed gas source 17 to the Venturi element 15. The control signal generated in response to the pressure in the vessel 5 exceeding the predefined pressure value is derived from the pressure sensor 10, which produces the control signal in response to the pressure monitored by the pressure sensor 10 being indicative of the pressure of the insufflating gas in the vessel 5 exceeding the predefined pressure value of approximately 25 mmHg. The control signal from the pressure sensor 10 is applied to the solenoid operated valve 19 in order to operate the solenoid operated valve 19 into the open state, to apply the compressed gas to the Venturi element 15, and to retain the solenoid operated valve 19 in the open state for so long as the control signal is being outputted by the pressure sensor 10. One of the externally generated control signals is produced by a foot operated switch 45, and the other one of the externally generated control signals is generated by a hand operated switch 46, and are both applied to the solenoid operated valve 19. The foot operated switch 45 may be operated by foot by a surgeon wishing to activate the Venturi vacuum creating device 14, in order to extract gas from the vessel 5 or to reduce the pressure of the insufflating gas in the vessel 5. The hand operated switch 46 may be operated by hand by a surgeon, likewise wishing to extract gas from the vessel 5 or to reduce the pressure of the insufflating gas in the vessel 5.

The foot operated switch 45 and the hand operated switch 46 are configured, so that when either one of them is operated into the closed state, a 12 volt or other suitable voltage supply is applied to the solenoid operated valve 19, in order to operate the solenoid valve 19 into the open state to apply the compressed gas to the Venturi element 15, and to retain the solenoid valve 19 in the open state for so long as either the foot operated switch 45 or the hand operated switch 46 is held in the closed state.

Turning now to the value of the force F1 applied by the compression spring 38 to the valving element 36, the forces acting on the valving element 36 as a result of a pressure drop across the valving element 36 in the direction of the arrow A are as follows:

$$FD=F2-F3$$

Where
  FD represents the force resulting from the pressure drop across the valving element 36,
  F2 represents the force of the insufflating gas from the vessel 5 acting on an upstream face 48 of the valving element 36, and
  F3 represents the force acting on a downstream face 49 of the valving element 36 by gas or air in the downstream valve chamber 32, which when the Venturi vacuum creating device 14 is active will be a negative force.

Since the pressure relief valve 27 is to operate from the closed state to the open state when the pressure drop across the valving element 36 exceeds the predefined pressure drop value of approximately 25 mmHg, the urging force F1 must therefore be equal to the force produced by the predefined pressure drop value of approximately 25 mmHg.

Therefore, $$F1=FD=F2-F3$$

$$F2=P_u \times A_d$$

$$F3=P_d \times A_d$$

Where

P$_u$ represents the pressure acting on the upstream face 48 of the valving element 36 from the upstream valve chamber 31 in the direction of the arrow A, A$_u$ represents the area of the valve orifice 34, which is substantially equal to the effective area of the upstream face 48 of the valving element 36, on which the pressure in the upstream valve chamber 31 acts, P$_d$ represents the pressure acting on the downstream face 49 of the valving element 36 in the direction of the arrow B, and A$_d$ represents the effective area of the downstream face 49 of the valving element 36 on which the downstream pressure P$_d$ acts.

Accordingly, $$F1=FD=P_u{\times}A_u-P_d{\times}A_u$$

Since, A$_d$ is approximately equal to A$_u$ $$F1=(P_u{\times}P_d)A_u$$

$$F1=(25\ \text{mmHg})A_u$$

In use, during insufflating of the vessel 5 by the insufflation system 1, the pressure relief valve 27 remains in the closed state until the pressure drop across the pressure relief valve 27 in the direction of the arrow A exceeds the value of the predefined pressure drop of 25 mmHg. The pressure drop across the pressure relief valve 27 can exceed 25 mmHg under two fundamental conditions. Firstly, when the Venturi vacuum creating device 14 is deactivated, and the pressure in the upstream chamber 31 of the pressure relief valve 27 exceeds 25 mmHg, which in this case would arise in the event of the pressure in the vessel 5 exceeding the predefined pressure value of 25 mmHg. Secondly, when the Venturi vacuum creating device 14 is activated by the control signal from either the pressure sensor 10 in the insufflator 3 or by the foot or hand operated switches 45 or 46, and the vacuum drawn in the Venturi throat 16 reaches a negative value, such that the sum of the difference of positive pressure in the vessel 5 and the negative vacuum pressure drawn by the Venturi vacuum creating device 14, taking into account the negative value of the vacuum pressure, results in a pressure drop equal to the predefined pressure drop value of 25 mmHg across the pressure relief valve 27.

In normal use, the value of the pressure P$_u$, namely, the pressure in the vessel 5 should not exceed 15 mmHg, and therefore, the pressure relief valve 25 will only open when the Venturi vacuum creating device 14 is activated. However, in the event of the pressure in the vessel 5 exceeding a pressure equal to the predefined pressure value of 25 mmHg, and if the pressure sensor 10 fails to produce the control signal, or if the Venturi vacuum creating device 14 fails to receive the control signal from the pressure sensor 10, or if the Venturi vacuum creating device 14 fails, the pressure relief valve 27 will operate from the closed state to the open state due to the pressure drop across the pressure relief valve 27 exceeding the predefined pressure drop value. Accordingly, the pressure relief valve 27 also acts as a failsafe device to relieve the pressure in the vessel 5, in the event of failure of the pressure sensor 10 or failure of the Venturi vacuum creating device 14.

Accordingly, the provision of the leak control system 26 according to the invention has many advantages. Firstly, the leak control system 26 prevents insufflating gas leaking through the Venturi vacuum creating device 14 when the Venturi vacuum creating device 14 is deactivated, unless the pressure in the vessel 5 exceeds the predefined pressure drop value. For so long as the pressure of the insufflating gas in the vessel 5 remains below the predefined pressure value of 25 mmHg, and the Venturi vacuum creating device 14 remains deactivated, the pressure relief valve 27 remains in the closed state, thereby preventing any leaking of the insufflating gas through the Venturi vacuum creating device 14. Therefore, the insufflating gas is only lost through the Venturi vacuum creating device 14 when insufflating gas is to be exhausted to atmosphere due to the excessive pressure of the insufflating gas in the vessel 5 or the surgeon wishes to evacuate smoke or other gases from the vessel.

Another and very important advantage of the invention is that in the event of the pressure of the insufflating gas in the vessel 5 increasing above the predefined pressure value of 25 mmHg, the pressure relief valve 25 is operated into the open state thereby permitting exhausting of insufflating gas from the vessel 5 and in turn through the Venturi vacuum creating device 14, even when the Venturi vacuum creating device 14 is deactivated. This is a particularly important advantage, since the pressure relief valve acts as a failsafe system which allows exhausting of the insufflating gas from the vessel 5 in the event of the pressure sensor 10 failing to produce the control signal to activate the Venturi vacuum creating device 14 in the event of the pressure of the insufflating gas in the vessel 5 exceeding the predefined pressure value of 25 mmHg, or in the event of the Venturi vacuum creating device 14 failing to receive the signal from the pressure sensor 10, or failure of the Venturi vacuum creating device 14.

Referring now to FIG. 4, there is illustrated a pressure relief valve of a leak control system according to another embodiment of the invention indicated generally by the reference numeral 50. Only the pressure relief valve 50 is illustrated. The leak control system is not illustrated but is substantially similar to the leak control system 26 described with reference to FIGS. 1 to 3 and also according to the invention. The pressure relief valve 50 is substantially similar to the pressure relief valve 27 described with reference to FIGS. 2 and 3, and similar components are identified by the same reference numerals. The only difference between the pressure relief valve 50 and the pressure relief valve 27 of FIGS. 2 and 3 is that the pressure relief valve 50 is adjustable for selectively adjusting the predefined pressure drop value at which the pressure relief valve 50 transitions from the closed state to the open state. In this embodiment of the invention the anchor means, against which the compression spring 38 acts for urging the valving element 36 into the closed state sealably engaging the valve seat 35, comprises an anchor plate 51 located in the downstream chamber 32 adjacent the downstream end wall 39.

A moving means, in this embodiment of the invention an adjusting screw 52 threadingly engaged in a threaded bore 53 in a nut 54 rigidly secured to the downstream end wall 39 of the valve housing 28, is manually operable for urging the anchor plate 51 in the direction of the arrows B and A towards and away from, respectively, the valving element 36, for in turn varying the force in the compression spring 38 with which the compression spring 38 acts on the valving element 36. By urging the anchor plate 51 from the downstream end wall 39 in the direction of the arrow B towards the valving element 36, the force F1, with which the compression spring 38 acts on the valving element 36 is increased, to thereby increase the predefined pressure drop value, at which the pressure relief valve transitions from the closed state to the open state. By urging the anchor plate 51 in the direction of the arrow A towards the downstream end wall 39 away from the valving element 36 reduces the force F1, with which the compression spring 38 acts on the valving element 36, to thereby reduce the predefined pressure drop value at which the pressure relief valve 50 transitions from the closed state to the open state. A hand grip knob 55 is provided on the adjusting screw 52 for facilitating manual operation of the adjusting screw 52. A graduated scale (not shown) is engraved on a flattened scale carrying surface for indicating the positions of the adjusting screw 52 relative to a datum face 56, which correspond to selectable predefined pressure drop values at which the valving element 36, and in turn the pressure relief valve transition from the closed state to the open state.

Once the adjusting screw 52 has been set so that the pressure relief valve 50 transitions from the closed state to the open state at the selected predefined pressure drop value, the pressure relief valve 50 is ready for use, and the operation of the pressure relief valve 50 in, for example, the evacuation system 12 is similar to that already described with reference to FIGS. 1 to 3.

Referring now to FIG. 5 there is illustrated an insufflation system according to another embodiment of the invention indicated generally by the reference numeral 60. The insufflation system 60 is substantially similar to the insufflation system 1 described with reference to FIGS. 1 to 3, and similar components are identified by the same reference numerals. The insufflation system 60 comprises an evacuation system, which is similar to the evacuation system 12, and a leak control system similar to the leak control system 26 also described in the insufflation system 1 of FIGS. 1 to 3, although the pressure relief valve 27 of the leak control system 26 may be replaced with the pressure relief valve 50.

The main difference between the insufflation system 60 and the insufflation system 1 is that an additional trocar 61 is illustrated extending into the vessel 5 for accommodating a surgical instrument, which in this embodiment of the invention comprises a cauterising instrument 63 for cauterising tissue, a lumen, vessel or organ in the vessel 5. The cauterising instrument 63 is illustrated in block representation and is controlled by a controller 65. An input interface 67 to the controller 65 allows a surgeon to control the operation of the cauterising instrument 63. Such cauterising instruments as the cauterising instrument 63 and their operation will be well known to those skilled in the art. A control signal output terminal 68 is provided from the controller 65 which provides a control signal indicative of activation of the cauterising instrument 63 for cauterising tissue, a lumen, vessel or organ in the vessel 5. The control signal from the output terminal 68 is applied to the solenoid valve 19, so that when the cauterising instrument 63 is being operated for cauterising, the solenoid valve 19 is operated into the open state. This in turn results in gas from the compressed gas source 17 being delivered through the Venturi element 15, for in turn developing a vacuum in the Venturi throat 16. Once the pressure drop across the pressure relief valve 27 exceeds the predefined pressure drop value, insufflating gas and smoke, generated by cauterising in the vessel 5, is drawn by the Venturi vacuum creating device 14 from the vessel 5.

On cauterising being completed, the control signal on the signal output terminal 68 is removed, thereby resulting in the solenoid valve 19 reverting to the closed state.

As well as, or in addition to the control signal from the control signal output terminal 68 of the controller 65 in response to activation of cauterising by the cauterising instrument 63, a surgeon may also operate either or both of the foot and hand operated switches 45 and 46 in order to maintain the solenoid valve 19 activated after the cauterising has been completed in order to remove any remaining smoke from the cavity.

Otherwise, the operation of the insufflation system 60 is similar to that described with reference to the insufflation system 1, and its use is likewise similar.

While the vacuum creating means has been described as comprising a Venturi vacuum creating device supplied with high velocity gas from a compressed gas source, any other suitable vacuum creating means besides a Venturi vacuum creating device may be used, for example, the vacuum may be generated by a vacuum pump. It will also be appreciated that while the insufflation system has been described as comprising a pressure sensor 10 for monitoring pressure in the vessel 5 for controlling the flow of insufflating gas to the vessel 5, and the pressure sensor 10 has also been described as producing a control signal for operating the solenoid valve 19, for in turn activating the Venturi vacuum creating device 14, while this is desirable, it is not essential. It will also be appreciated that any other suitable activating means may be provided for activating the Venturi vacuum creating device or other vacuum creating device.

Needless to say, it will be appreciated that in some embodiments of the invention only one of the foot pedal switch and the hand operated switch may be provided for activating the vacuum creating device.

It is also envisaged that the solenoid operated valve 19 may be responsive to activation of any surgical instrument besides a cauterising instrument located in the vessel for activating the Venturi vacuum creating device or other vacuum creating device. It is also envisaged that the signal applied to the solenoid operated valve 19 in response to activation of the cauterising instrument could be time delayed for a few seconds after the commencement of operation of the cauterising instrument, so that the Venturi vacuum creating device would only be activated when smoke resulting from cauterisation is generated. It is also envisaged that the solenoid operated valve typically would be retained in the open state for a short time delay after the cauterising instrument had been deactivated in order to ensure the removal of all smoke generated by cauterising. Needless to say, the solenoid operated valve 19 may be responsive to the activation of other instruments operating within the vessel 5 which may produce smoke or other gases which should be extracted, such as nitrogen gas which would result from freezing of tissue in the vessel 5, or another vessel, lumen or organ in the vessel 5.

While a filter has been described as being located in the evacuating conduit 20, while this is desirable, it is not essential. It will also be appreciated that any other suitable pressure relief valve may be provided, instead of the pressure relief valve described. For example, it is envisaged that the pressure relief valve may be of the type whereby a tension spring may be located in the upstream valve chamber that would act to pull the valving element into engagement with the valve seat instead of the valving element being pushed into engagement with the valve seat 36. It is also envisaged that the valving element would be provided with a central spindle extending from the valving element in the upstream direction through the valve seat into the upstream valve chamber, and a compression spring would be provided on the central spindle acting between the partition wall, and an abutment member located on the central spindle spaced apart in an upstream direction from the valving element.

While the high velocity gas delivered through the Venturi element has been described as being supplied by a compressed gas source, any suitable compressed gas source may be provided, for example, a compressed air source or a compressed carbon dioxide source, or indeed any other suitable compressed gas source.

While the leak control system has been described as being provided in an overall insufflation system, it is envisaged that the leak control system according to the invention may be provided independently of the insufflation system, and would be provided to be suitable for connecting to an insufflation system.

Additionally, while the leak control system has been described for locating in an evacuation system, it is also envisaged that the leak control system may be provided separately from the evacuation system, and would be provided to be suitable for connecting into an evacuation system of an insufflation system.

Furthermore, it is envisaged that while the evacuation system has been described as being provided in an insufflation system, it is envisaged that the evacuation system may be supplied on its own and would be provided to be suitable for connecting into an insufflation system.

It is also envisaged that any other suitable valve besides a solenoid valve may be provided for applying the pressurised gas from the compressed gas source to the Venturi element.

It is also envisaged that any other suitable compressed gas source or indeed high velocity gas generating system may be provided instead of the compressed gas source.

The invention claimed is:

1. An evacuation system for an insufflation system, the evacuation system comprising:
   a vacuum creating means,
   a flow path communicating the vacuum creating means with a vessel of a subject being insufflated by the insufflation system for accommodating insufflating gas from the vessel, and
   a leak control system adapted for minimising leakage of insufflating gas from the vessel through the flow path when the evacuation system is deactivated, the leak control system comprising:
   a pressure relief valve located in the flow path upstream of the vacuum creating means, the pressure relief valve being operable from a closed state preventing gas flow to the vacuum creating means through the flow path, to an open state permitting gas flow to the vacuum creating means through the flow path, in response to a pressure drop across the pressure relief valve in the direction of flow to the vacuum creating means exceeding a predefined pressure drop value.

2. The evacuation system as claimed in claim 1 in which the vacuum creating means comprises a Venturi vacuum creating device, and the flow path for accommodating the insufflating gas from the vessel terminates in a vacuum generating throat of the Venturi vacuum creating device.

3. The evacuation system as claimed in claim 1 in which the vacuum creating means is responsive to a signal generated in response to pressure in the vessel being insufflated exceeding a predefined pressure value, or an externally generated signal.

4. The evacuation system as claimed in claim 3, in which the externally generated signal comprises one of a manually generated signal, or a signal generated in response to activation of a surgical instrument.

5. The evacuation system as claimed in claim 4 in which the signal generated in response to activation of a surgical instrument is generated in response to a surgical instrument located in the vessel.

6. The evacuation system as claimed in claim 4 in which the signal generated in response to activation of a surgical instrument is generated in response to a cauterising instrument being activated, or freezing instrument being activated.

7. The evacuation system as claimed in claim 6 in which the freezing instrument comprises an instrument configured to deliver a liquid gas to a site to be frozen.

8. The evacuation system as claimed in claim 4 in which the manually generated signal is generated by one or both of a foot operable switch and a hand operable switch.

9. The evacuation system as claimed in claim 3 in which the predefined pressure value of the pressure in the vessel lies in the range of 5 mmHg to 50 mmHg.

10. The evacuation system as claimed in claim 3 in which the signal generated in response to the pressure in the vessel being insufflated exceeding the predefined pressure is produced by the insufflation system.

11. The evacuation system as claimed in claim 1 in which the vacuum creating means is configured to generate a vacuum down to at least 30 mmHg below atmospheric pressure.

12. The evacuation system as claimed in claim 1 in which the pressure relief valve comprises a valve seat defining a valve orifice therethrough for accommodating gas therethrough to the vacuum creating means, and a valving element operable between a closed state sealably engaging the valve seat to close the valve orifice with the valve in the closed state, and an open state spaced apart from the valve seat to open the valve orifice with the valve in the open state.

13. The evacuation system as claimed in claim 12 in which the valving element is urgeable into the closed state by an urging means acting against the direction of flow to the vacuum creating means.

14. The evacuation system as claimed in claim 12 in which the pressure relief valve comprises a housing defining a hollow interior region, a partition wall located in the hollow interior region of the housing dividing the hollow interior region into an upstream valve chamber and a downstream valve chamber, the valve orifice being formed in the partition wall and communicating the downstream valve chamber with the upstream valve chamber, an inlet port to the upstream valve chamber configured for connecting to the flow path on the upstream side of the pressure relief valve, and an outlet port from the downstream valve chamber configured for connecting to the flow path on the downstream side of the pressure relief valve.

15. The evacuation system as claimed in claim 1 in which an evacuating conduit is provided defining the flow path and terminating in an upstream end configured for receiving the insufflating gas from a vessel being insufflated, the evacuating conduit being configured for communicating with the vacuum creating means, and the pressure relief valve is located in the evacuation conduit.

16. The evacuation system as claimed in claim 1 in which the predefined pressure drop value lies in the range of 5 mmHg to 1000 mmHg.

17. The evacuation system as claimed in claim 1 in which the predefined pressure drop value lies in the range of 10 mmHg to 500 mmHg.

18. An insufflation system for supplying an insufflating gas to a vessel of a subject for insufflating thereof, the insufflation system comprising:
   an insufflator for insufflating the vessel of the subject with the insufflating gas and for controlling a flow rate of the insufflating gas to the vessel, and an evacuation system for evacuating insufflating gas from the vessel, the evacuation system comprising:

a vacuum creating means, a flow path communicating the vacuum creating means with the vessel for accommodating insufflating gas from the vessel, and a leak control system adapted for minimising leakage of insufflating gas from the vessel through the flow path of the evacuation system when the evacuation system is deactivated, the leak control system comprising:

a pressure relief valve located in the flow path of the evacuation system upstream of the vacuum creating means, the pressure relief valve being operable from a closed state preventing gas flow to the vacuum creating means through the flow path, to an open state permitting gas flow to the vacuum creating means through the flow path, in response to a pressure drop across the pressure relief valve in the direction of flow to the vacuum creating means exceeding a predefined pressure drop value.

19. An evacuation system for an insufflation system, the evacuation system comprising:

a vacuum creating means, a flow path communicating the vacuum creating means with a vessel being insufflated by the insufflation system for accommodating insufflating gas from the vessel, and a leak control system adapted for minimising leakage of insufflating gas from the vessel through the flow path, the leak control system comprising:

a pressure relief valve located in the flow path upstream of the vacuum creating means, the pressure relief valve being operable from a closed state preventing gas flow to the vacuum creating means through the flow path, to an open state permitting gas flow to the vacuum creating means through the flow path, in response to a pressure drop across the pressure relief valve in the direction of flow to the vacuum creating means exceeding a predefined pressure drop value, the pressure relief valve comprising:

a valve seat defining a valve orifice therethrough for accommodating gas therethrough to the vacuum creating means, a valving element operable between a closed state sealably engaging the valve seat to close the valve orifice with the valve in the closed state, and an open state spaced apart from the valve seat to open the valve orifice with the valve in the open state, an urging means configured to urge the valving element into the closed state with a force sufficient to maintain the valving element in the closed state until the pressure drop across the valving element in the direction of flow to the vacuum creating means exceeds the predefined pressure drop value, and an anchoring means engageable with the urging means with the urging means acting between the anchoring means and the valving element to urge the valving element into the closed state, the anchoring means being moveable relative to the valving element for varying the force with which the urging means urges the valving element into the closed state, to in turn selectively adjust the predefined pressure drop value to which the pressure relief valve is responsive.

20. The evacuation system as claimed in claim 19 in which a means for moving the anchoring means relative to the valving element for varying the spacing between the anchoring means and the valving element.

* * * * *